US005368045A

United States Patent [19]
Clement et al.

[11] Patent Number: 5,368,045
[45] Date of Patent: Nov. 29, 1994

[54] BIOPSY NEEDLE INSTRUMENT

[75] Inventors: Thomas P. Clement; James S. Bates, both of Bloomington; Darrell W. White, Spencer, all of Ind.

[73] Assignee: Boston Scientific Corporation, Watertown, Mass.

[21] Appl. No.: 583,080

[22] Filed: Sep. 14, 1990

Related U.S. Application Data

[63] Continuation-in-part of Ser. No. 381,780, Jul. 18, 1989, Pat. No. 4,958,625.

[51] Int. Cl.⁵ .............................................. A61B 10/00
[52] U.S. Cl. .................................. 128/754; 128/749
[58] Field of Search ..................... 128/749, 751–754; 606/167, 170

[56] References Cited

U.S. PATENT DOCUMENTS

| | | |
|---|---|---|
| 1,867,624 | 7/1932 | Hoffman . |
| 3,175,554 | 3/1965 | Stewart . |
| 3,595,217 | 7/1971 | Rheinfrank . |
| 3,995,619 | 12/1975 | Glatzer . |
| 4,178,810 | 12/1979 | Takahashi . |
| 4,402,324 | 9/1983 | Lindgren et al. . |
| 4,461,305 | 7/1984 | Cibley . |
| 4,476,864 | 10/1984 | Tezel . |
| 4,570,632 | 2/1986 | Woods . |
| 4,600,014 | 7/1986 | Beraha . |
| 4,609,370 | 9/1986 | Morrison . |
| 4,685,904 | 8/1987 | Krebs . |
| 4,699,154 | 10/1987 | Lindgren . |
| 4,702,261 | 10/1987 | Cornell et al. . |
| 4,733,671 | 3/1988 | Mehl . |
| 4,735,215 | 4/1988 | Goto et al. . |
| 4,766,907 | 8/1988 | de Groot et al. . |
| 4,790,329 | 12/1988 | Simon . |
| 4,881,551 | 11/1989 | Taylor . |
| 4,893,635 | 1/1990 | de Groot et al. . |
| 4,903,709 | 2/1990 | Skinner . |
| 4,944,308 | 7/1990 | Akerfeldt ............. 128/751 |
| 4,953,558 | 9/1990 | Akerfeldt ............. 128/751 |

FOREIGN PATENT DOCUMENTS 010321 10/1979 European Pat. Off. .

(List continued on next page.)

OTHER PUBLICATIONS

Lindgren, "Percutaneous Needle Biopsy—A New Technique", ACTA Radiologica Diagnosis, Nov. 1982, pp. 653–656.

(List continued on next page.)

Primary Examiner—Robert A. Hafer
Assistant Examiner—Sam Rimell
Attorney, Agent, or Firm—Fish & Richardson

[57] ABSTRACT

One-handed operable biopsy needle instruments, employing combined spring driven stylets, and cannulas, capable of taking multiple specimens while the other hand is free, e.g. to manipulate an ultrasound probe are described. The particular biopsy needle instrument shown in detail has a pair of cannula and stylet compression springs, a pair of members directly engaged on the ends of the springs mounting respectively the cannula and stylet, and releasable holding means for holding the springs compressed until firing. The device that loads the stylet spring and a pivotal latch each can serve as a means for releasably holding the stylet spring. A latch is employed to releasably hold the cannula spring. Actuation of the stylet can cause sequential operation of the cannula through impact of the stylet-mounting member on the cannula latch. Finger-displaceable means provided on a side surface of the housing for selective loading of the springs, and provision of finger-displaceable lock and firing button, all operable by a hand while that hand holds the device, enables single-handed loading and taking of the biopsy specimen(s). The embodiment shown employs a pair of longitudinally arranged, recessed thumb-actuated slide switches on a broad side of a rectangular cross-section housing, and lock and firing button on top, in pre-arranged relationship to the bevel of the stylet tip.

23 Claims, 9 Drawing Sheets

FOREIGN PATENT DOCUMENTS

| | | |
|---|---|---|
| 0010321 | 4/1980 | European Pat. Off. . |
| 0207726 | 1/1987 | European Pat. Off. . |
| 141108 | 1/1950 | Germany . |
| 48382 | 2/1970 | Germany . |
| 141108 | 4/1980 | Germany . |
| 483829 | 2/1970 | Switzerland . |
| 175611 | 10/1965 | U.S.S.R. . |
| WO83/00112 | 1/1983 | WIPO . |
| WO8300112 | 1/1983 | WIPO . |
| WO83/03343 | 10/1983 | WIPO . |

OTHER PUBLICATIONS

PCT International Search Report, From WO 83/00112, Jan. 1983.

Microvasive—Brochure, Van Tec Products.

Radiplast Biopty—Brochure, Radiplast AB Sweden.

Travenol—True Cut Disposable Biopsy Needle, Travenol Laboratories.

Meditsch Brochure, "Introducing Biopty Automatic Biopsy System", Jul. 1986.

Van-Tech Products, Micro Vasive, Products for Endourology, "Single Puncture Prostatic Biopsy Needle".

BIOPSY NEEDLE INSTRUMENT

BACKGROUND OF THE INVENTION

This is a continuation-in-part patent application of U.S. Ser. No. 381,780, filed Jul. 18, 1989, now U.S. Pat. No. 4,958,625.

The invention relates to the field of surgical biopsy instruments.

A biopsy instrument is frequently used to obtain a piece of tissue for microscopic examination to determine malignancy, while subjecting the patient to the least trauma. Typically, the instrument consists of a long, thin probe, termed a stylet, within a close-fitting hollow needle, termed a cannula. The stylet and cannula are contained within a firing device that first projects the stylet into the tumor, followed immediately by the cannula. The stylet has a notch into which tissue will prolapse when the stylet enters the tumor. As the cannula slides over the stylet, a small piece of tissue is then severed from the tumor mass and captured within the notch of the stylet. The instrument is then withdrawn and the piece of tissue removed from the stylet.

Lindgren, U.S. Pat. No. 4,699,154, describes a biopsy needle instrument which projects the stylet and the cannula sequentially when the firing button is pushed. That instrument requires that the physician load both the stylet and the cannula at the same time by compressing the stylet and cannula springs simultaneously.

SUMMARY OF THE INVENTION

According to one aspect, the invention provides one-handed operable biopsy needle instruments, employing combined spring driven stylets and cannulas, capable of taking multiple specimens while the other hand is free, e.g. to manipulate an ultrasound probe.

According to one aspect, the invention provides biopsy instruments that are simple, relatively inexpensive to fabricate of plastic parts, suitable for one-time use and disposability, and, importantly, which achieve all of this in an instrument capable of one-handed operation.

Preferred embodiments incorporate slide means that enable one-handed, selective loading of cannula and stylet springs, locking and firing. Simple molded members, one directly on the end of each spring, mount respectively the cannula and needle, and provide formations that directly receive the loading force. In the preferred embodiments, this force is applied by direct thumb-operated projections on the side of the housing and pivotable latches are provided for each spring for latching and releasing the springs.

In one embodiment of the invention, the biopsy needle instrument comprises a selectable locking means, movable between two positions including a first safety position to prevent projection of the stylet and cannula, and a second position to permit projection of the stylet and the immediate sequential projection of the cannula.

In another embodiment, the biopsy needle comprises a selectable locking means movable also to a third or intermediate position which allows the stylet to be projected separately from the cannula. This arrangement permits a user to determine if the stylet is in the correct location prior to projecting the cannula. In this way, if the stylet misses the tumor, the cannula is not projected, thereby avoiding unnecessary damage to healthy tissue.

Another aspect of the embodiments is the ability to load the cannula and stylet separately, and yet fire them sequentially using a single button. In this way, the physician is not required to work simultaneously against two stiff springs in loading the instrument for use.

BRIEF DESCRIPTION OF THE DRAWINGS

This invention is pointed out with particularity in the appended claims. The above and further advantages of this invention may be better understood by referring to the following description taken in conjunction with the accompanying drawings in which:

FIG. 1a is a side view of the biopsy needle instrument of FIG. 1 in which the stylet and cannula are projected automatically in succession, while FIG. 1b is a top view of the instrument of FIG. 1, and FIG. 1c is an enlarged view of the forward end of the cannula and stylet of FIG. 1;

FIG. 2 is a cross-sectional view taken at A—A of FIG. 1a;

in FIG. 4b the selector switch is in position to fire the stylet separately from the cannula and the stylet is firing; in FIG. 4c the stylet fully projected, and in FIG. 4d the selector switch is in position to fire the cannula and the cannula is firing.

DESCRIPTION OF THE PREFERRED EMBODIMENTS STRUCTURE

Figure 1:
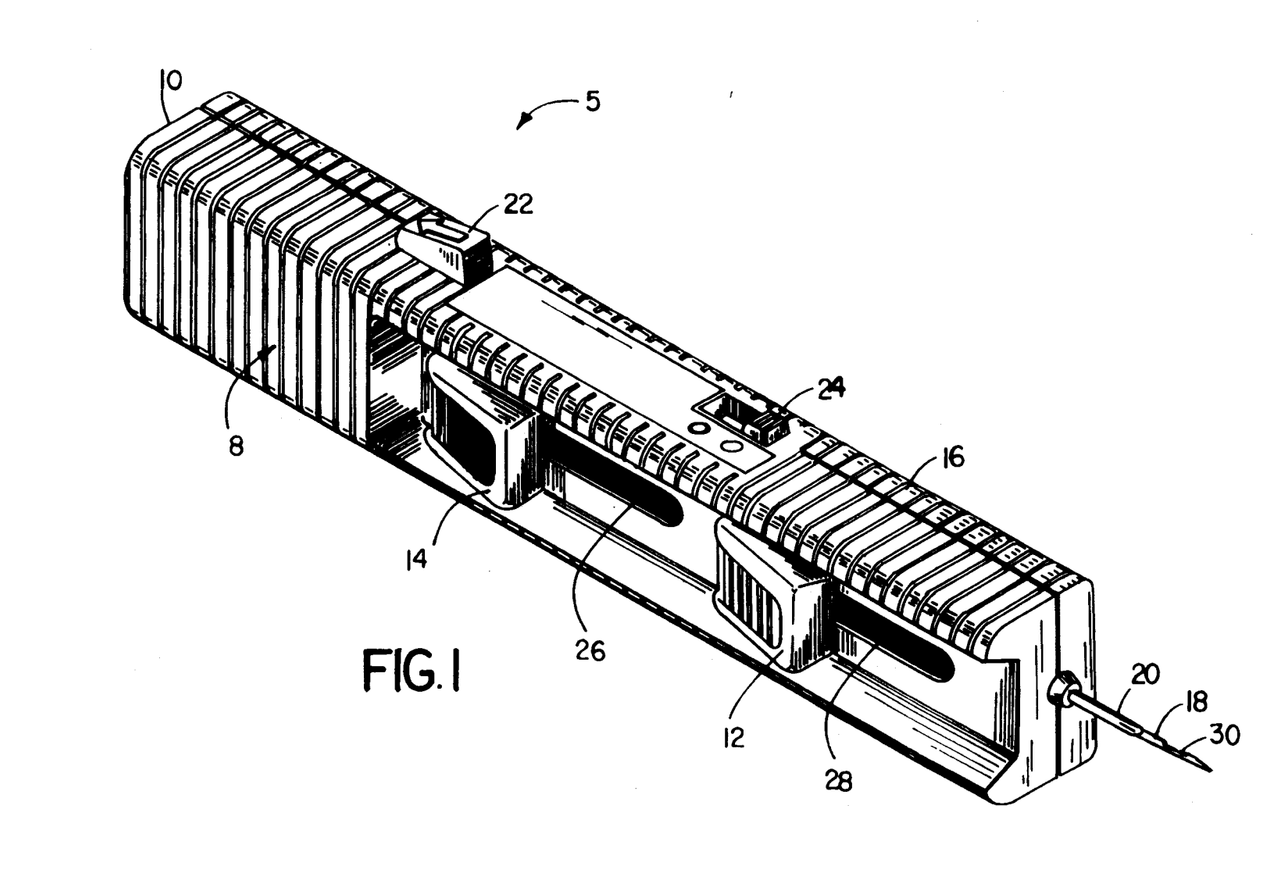
FIG. 1 is a perspective view of an embodiment of the biopsy needle instrument of the invention.

Referring to FIG. 1, a biopsy needle instrument 5 of the invention has a housing 8, consisting of an upper housing 10 and a lower housing 16. Stylet 18 and cannula 20 project from housing 8. Forward loading slide switch 12 and rearward loading slide switch 14 protrude from the upper housing and are constrained to move within slots 26, 28. A firing button 22 and a selector switch 24 also project from the housing 8.

Figures 1A, 1B, 1C:
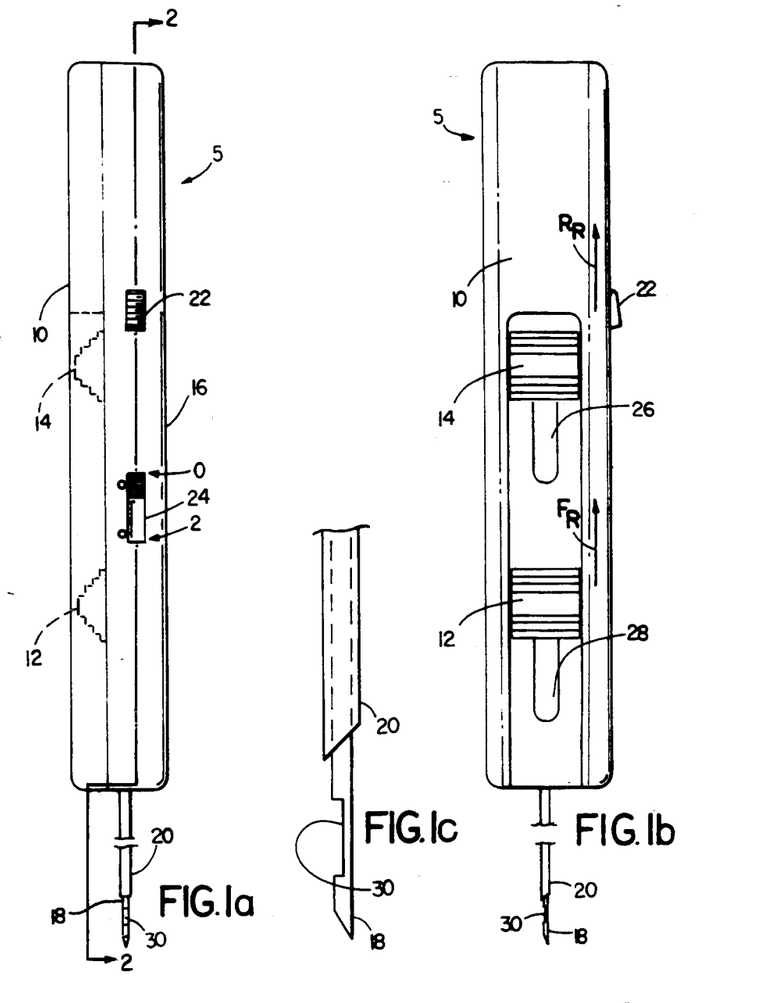

Referring to FIGS. 1(a) and (b), when the stylet 18 is to be loaded for firing, the rear loading slide switch 14, attached to the stylet 18, is slid rearwardly (arrow $R_R$) within a slot 26. When the stylet 18 is fired, the rear loading slide switch 14 moves forwardly within the slot.

Similarly, when the cannula 20 is to be loaded for firing, the forward loading slide switch 12, attached to the cannula 20, is slid rearwardly (arrow $F_R$) within slot 28. When the cannula 20 is fired, the forward loading slide switch 12 moves forwardly within the slot.

Figure 2:
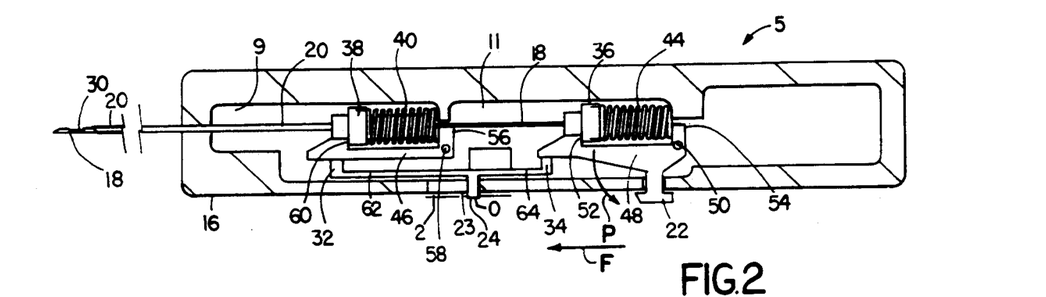

FIG. 2 shows the instrument firing mechanism positioned within the lower housing 16. Stylet 18 is located coaxially within cannula 20, and the forward end of each projects through the forward end of the lower housing 16. The rearward end of cannula 20 attaches to the cannula retaining collar 38 which is biased forward (arrow F) by spring 40. The cannula retaining collar 38 and spring 40 are located within a forward cavity 9 of the lower housing 16. The rearward end of the spring 40 rests against the rear lever 56 of the forward rocker arm 46 and is held in the compressed state by engagement of the cannula retaining collar 38 by the latch portion 60 of the forward rocker arm 46. The forward rocker arm 46 is prevented from pivoting about the pin 58 (thereby releasing cannula retaining collar 38 and spring 40) when the selector switch 24 is in the position designated as "0" by a forward restraining projection 32 of forward arm 62 of the selector switch 24.

The rearward end of the stylet 18 extends through cannula 20, cannula retaining collar 38, and spring 40 and is attached to a stylet retaining collar 36 which is biased forward (arrow F) by spring 44. The stylet retaining collar 36 and spring 44 are located within a rearward cavity 11 of the lower housing 16. The rearward end of spring 44 rests against the rear lever 54 of the rearward rocker arm 48 and is held in the compressed state by engagement of the stylet retaining collar 36 by the latch portion 52 of the rearward rocker arm 48. The rearward rocker arm 48 is prevented from pivoting about the pin 50 (and thereby releasing stylet retaining collar 36 and spring 44) when the selector switch 24 is in the position designated as "0" by a rearward restraining projection 34 of the rearward arm 64 of the selector switch 24.

As the selector switch 24 is moved forward to the position designated "2", the forward restraining projection 32 is moved forward away from the forward rocker arm 46. Rear restraining projection 34 is simultaneously moved forward away from the rearward rocker arm 48. The rearward rocker arm 48 is thus free to pivot counterclockwise (arrow P) about pin 50. The forward rocker arm 46 is also free to pivot counterclockwise.

Operation

Figure 3A:
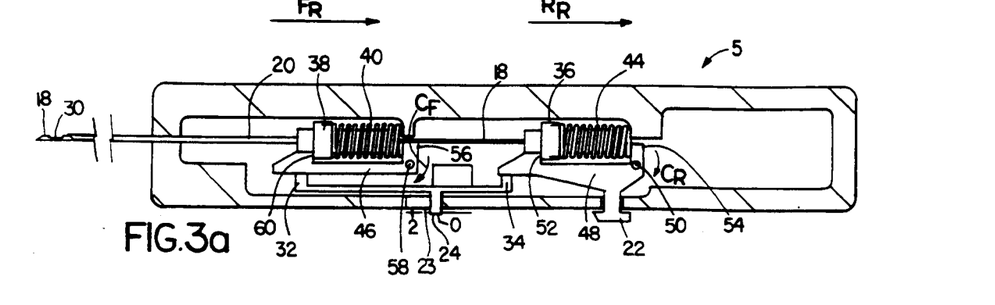
FIG. 3a is a cross-sectional view of the instrument of FIG. 2 with the selector switch set to a first safety position.

Referring also to FIG. 3a et seq., and FIG. 1b, with the selector switch 24 placed in position "2" (FIG. 3d), the cannula 20 is loaded by moving the front loading slide switch 12 rearwardly (arrow $F_R$). The front loading slide switch 12 is attached to the cannula retaining collar 38, and as the front loading slide switch is moved rearwardly, the cannula retaining collar 38 is also moved rearwardly and spring 40 is compressed. The compression puts pressure against rear lever 56 of the forward rocker arm 46 causing it to rotate clockwise (arrow $C_F$) about pin 58. This also causes the forward rocker arm 46 to rotate clockwise until the latch portion 60 of the forward rocker arm 46 engages the cannula retaining collar 38. At this point the cannula 20 is loaded for firing.

The stylet 18 is then loaded by moving the rear loading slide switch 14 rearwardly (arrow $R_R$). The rear loading slide switch 14 is attached to the stylet retaining collar 36, and as the rear loading slide switch 14 is moved rearwardly, spring 44 is compressed. The compression puts pressure against rear lever 54 of the rearward rocker arm 48 causing it to rotate clockwise (arrow $C_R$) about pin 50. This also causes the rearward rocker arm 48 to rotate clockwise until the latch portion 52 of the rearward rocker arm 48 engages the stylet retaining collar 36. At this point the stylet 18 is also loaded for firing. The selector switch is then moved to position "0" (FIG. 3a) so the restraining projections 32 and 34 of the selector switch 24 prevent the cannula 20 and stylet 18 respectively from being accidentally fired.

A benefit of the separately loadable cannula and stylet is that to load the device, only one spring need be compressed at a time, thereby significantly reducing the amount of effort required.

Figure 3B:
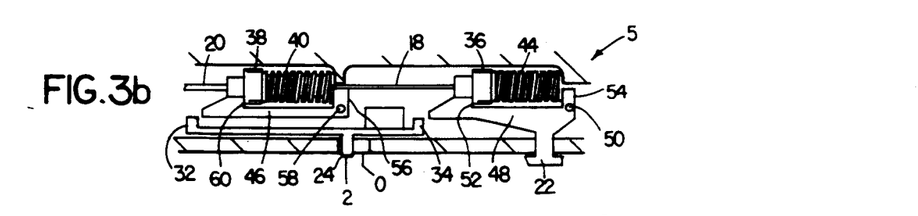
FIG. 3b is the cross-sectional view of the firing mechanism of the instrument of FIG. 3a with the selector switch set to project both the stylet and the cannula.

Referring to FIG. 3b, to fire the stylet 18 and the cannula 20 in quick succession, the selector switch 24 is moved forward to position "2" moving the restraining projections 32, 34 forward away from the rocker arms 46, 48 respectively. In this position both the forward 46 and rearward 48 rocker arms can rotate freely about the pins 58 and 50 respectively.

Figure 3C:
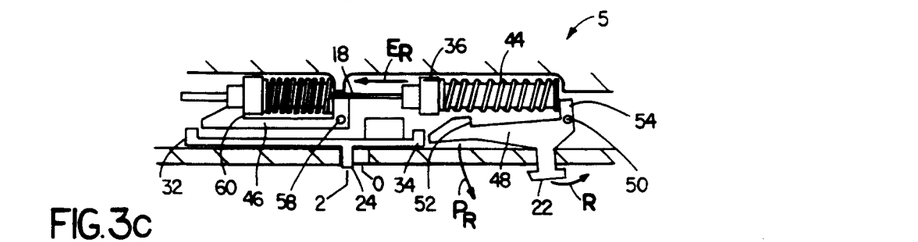
FIG. 3c is a similar view with the stylet firing.

Referring to FIG. 3c, when the firing button 22 is pressed rearwardly (arrow R), the rocker arm 48 rotates counter-clockwise (arrow $P_R$) about pin 50 causing latch portion 52 of the rocker arm 48 to be pulled away from the stylet retaining collar 36. This allows spring 44 to expand and project the stylet retaining collar 36 and stylet 18 forward (arrow $E_R$).

Figure 3D:
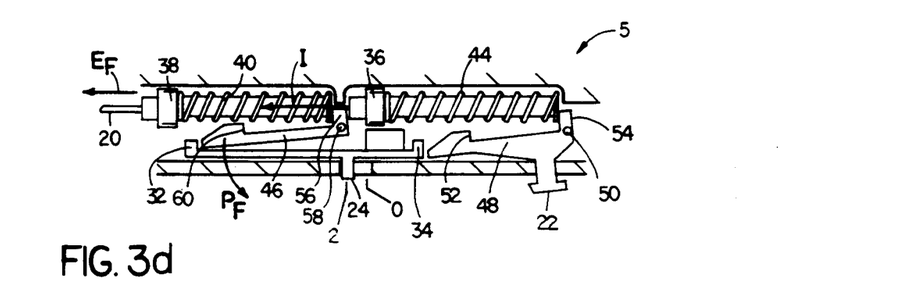
FIG. 3d is a similar view with the cannula firing.

Referring to FIG. 3d, as spring 44 expands, it propels the stylet retaining collar 36 against the rear lever 56 of the forward rocker arm 46. The momentum of the stylet retaining collar 36 forces the rear lever 56 forward (as shown by arrow I) and causes forward rocker arm 46 to rotate counter clockwise (arrow $P_F$) about pin 58. As the rocker arm 46 rotates, it pulls the latch portion 60 of rocker arm 46 away from the cannula retaining collar 38. This releases the spring 40 and projects collar 38 and cannula 20 forward (arrow $E_F$).

It may help the reader who is unfamiliar with such biopsy devices to have a more graphic explanation as to how the device may be used in practice.

Figure 6:
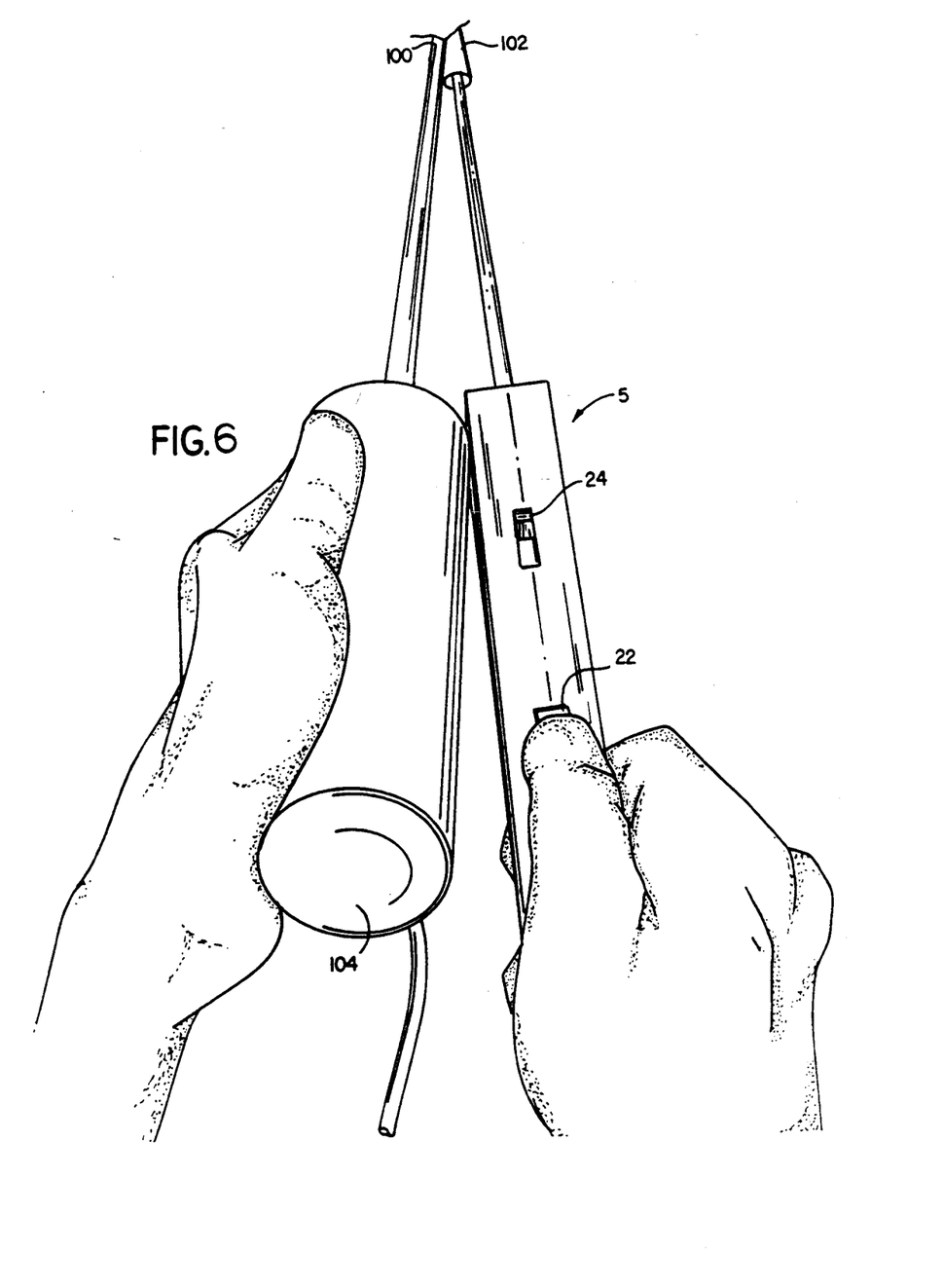
FIG. 6 is a diagrammatic perspective view of the biopsy instrument in firing position alongside an ultrasonic probe, each being held by a single hand of the physician.
Figure 7:
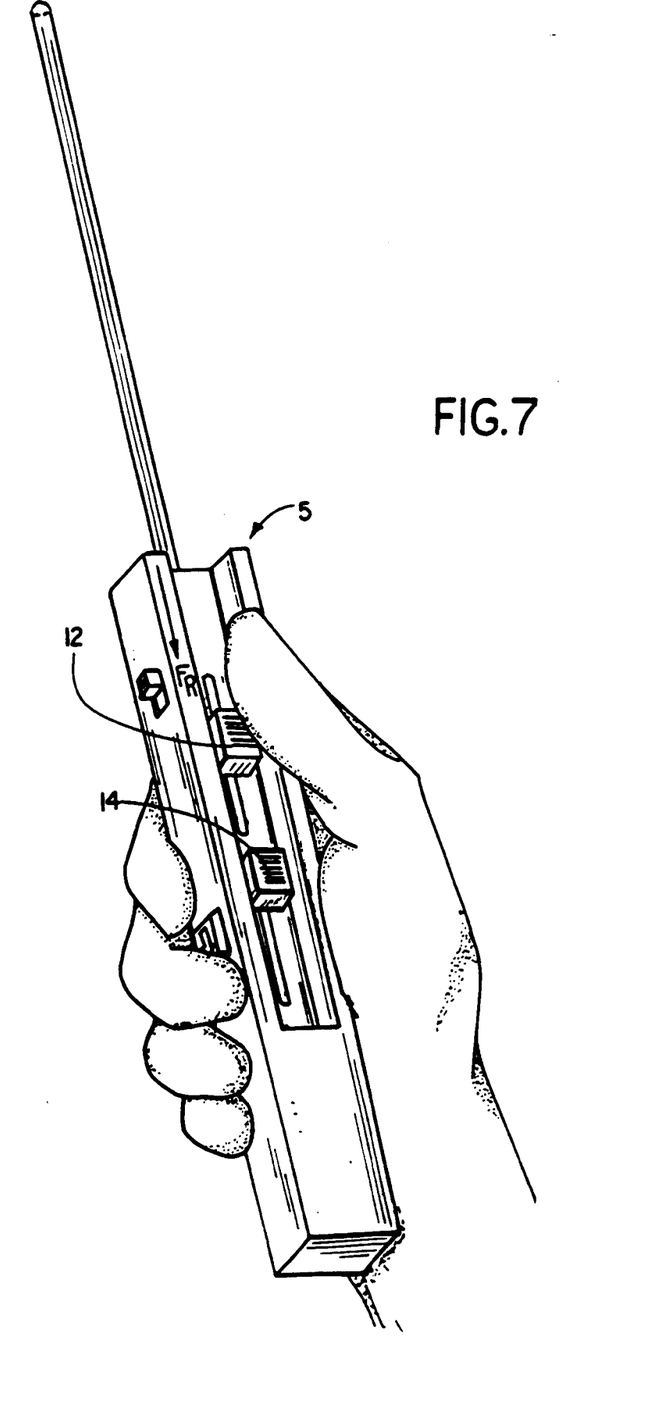
FIG. 7 is a perspective view illustrating one-handed loading of the forward cannula spring.
Figure 8:
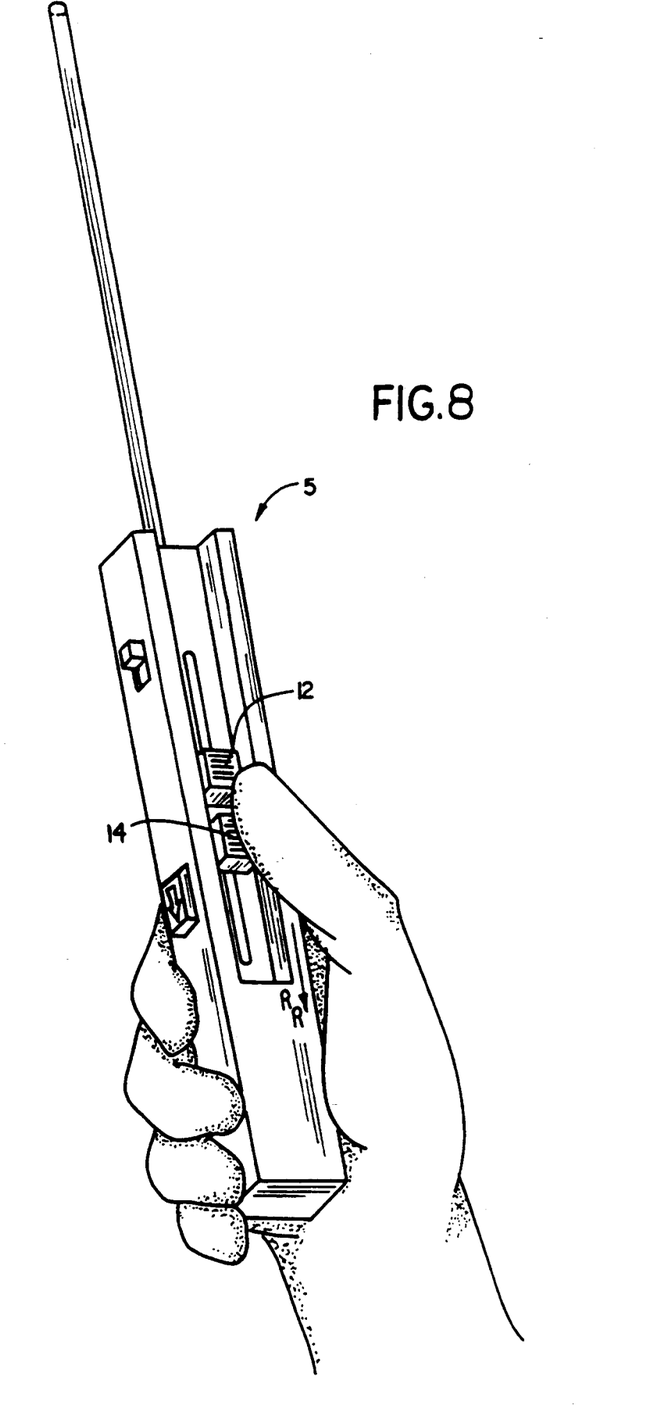
FIG. 8 is a similar perspective view illustrating one-handed loading of the rear stylet spring.
Figure 9:
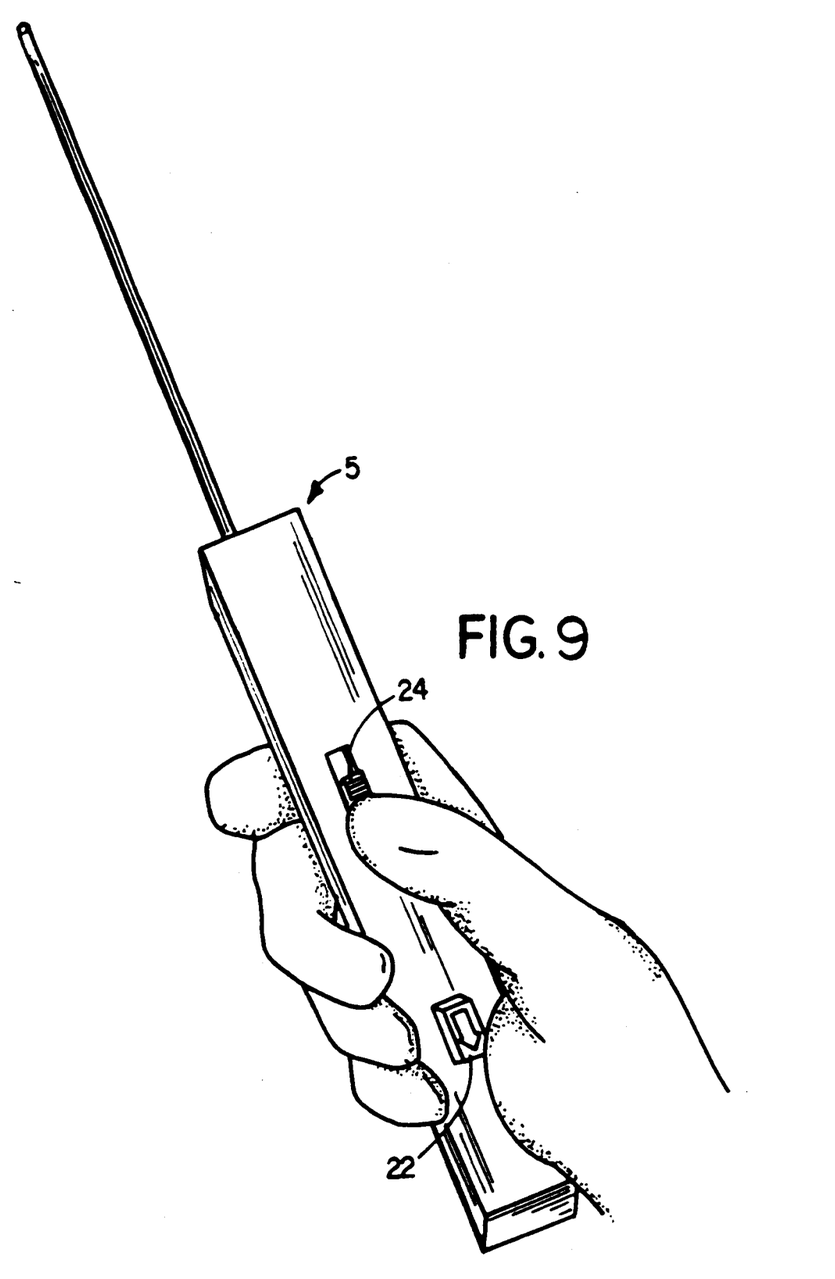
FIG. 9 is another perspective view illustrating one-handed adjustment of the hand on the instrument to expose the locking slide and firing button.

As is well known to the field, a typical use is in examination of the prostate by transrectal ultrasonic imaging. Typically the physician inserts into the rectum an ultrasonic probe 100, FIG. 6, and examines the prostate by viewing an ultrasound image on a viewing screen. (At this stage the biopsy device 5 shown in FIG. 6 is not present.) If, during this examination, the physician detects a suspicious region for which biopsy is advisable, an attendant is requested to provide a biopsy device 5. Typically the attendant opens a sterile pack and provides the device to the physician in unloaded condition, as it comes sterile from the manufacturer. The physician then, while holding the ultrasonic probe handle 104 so as to maintain the probe in the rectum with one hand (the "ultrasound" hand) grasps the biopsy device 5 with the other hand and proceeds to load the biopsy device. The sequence of FIGS. 7 through 9 show this graphically. As shown in FIG. 7, the physician first grasps the device so that his thumb, in extended position, engages forward cannula switch 12, and he pulls back with his thumb in direction $F_R$, FIGS. 1b and 3a, while grasping the handle with the base of the same hand, until spring 40 is compressed and the latch portion 60 of forward rocker arm 46 moves into latched position. Thereupon, while still holding the handle one handedly, the physician works the "biopsy" hand rearwardly to the position of FIG. 8, likewise engages rearward loading switch 14 and compresses spring 44 by movement in direction $R_R$, FIGS. 1b and 3a. While in theory the physician need not reach the fully compressed position for rear spring 44 (he or she could hold it under tension by his or her thumb while inserting the device and when in position release it to cause sequential firing), the device of FIG. 1 is designed so that the physician may fully load spring 44 until latch portion 52 of rearward rocker arm 48 moves into latched position. At this point, if desired, the physician may lock the device in loaded position with the same hand by sliding the selector switch 24 to locking position.

Figure 5:
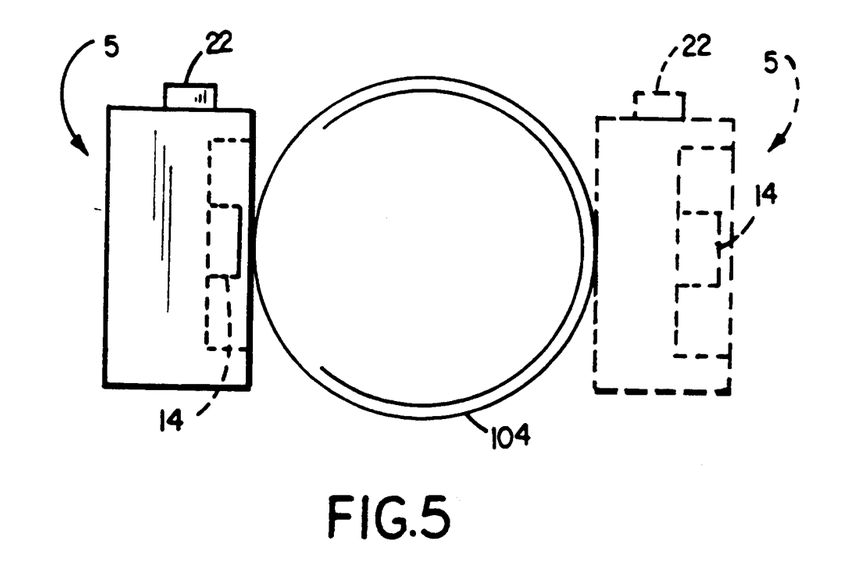
FIG. 5 is a diagrammatic endview showing possible positions of the handle of the biopsy instrument relative to an ultrasonic probe with which it is used.

With the device locked or not, as desired, the physician, still using the one "biopsy" hand, inserts the biopsy device into the rectum through the particular biopsy channel 102 provided by the particular ultrasound probe 100 being employed. This channel may be on the left or right side of the probe of the ultrasonic instrument, or may extend down a channel within the ultrasonic probe. FIG. 5 discloses the position the biopsy device may take in right or left positions, with a respective side face (broad dimension), of the handle lying closely along-side the handle 104 of the ultrasound device. (The recessed nature of the loading slide switches 12, 14, in the biopsy handle as shown in FIGS. 1, 1a and 1b, allow this close relationship shown in solid lines to be obtained without interference with the slide switches.) Thus the needle and the probe can extend closely along-side each other into the rectum, as shown in FIG. 6.

Thereafter the physician may manipulate the ultrasound device with one hand and the biopsy needle device with the other while watching the viewing screen, until the biopsy needle is brought to the desired position. Then, if needed and not already done, the physician uses a finger of the "biopsy" hand to slide the selector switch to firing position, and then with a finger or thumb of the hand engages the firing button 22 to fire the device. All actions can thus be accomplished with the one "biopsy" hand. The construction of the device enables the physician to always orient the narrow side of the handle carrying the firing button upwardly, regardless of which relationship the biopsy handle has to the ultrasonic device. Advantageously, as shown in FIG. 1, the bevel of the stylet is pre-arranged to face left when the firing button is up (the loading switches always facing right). By this means, merely by assuring the firing button is up, the physician can be sure of the correct orientation of the stylet bevel to the tissue to be penetrated.

Following firing, still with the ultrasonic probe held in position with the physician's "ultrasound" hand, the physician, with the "biopsy" hand, withdraws the instrument from the rectum, retracts the cannula and delivers the biopsy specimen to the attendant for immediate transmittal to the laboratory. The physician may now readily repeat the procedure of loading, repositioning and firing the instrument to obtain multiple specimens, all one handedly.

When the biopsy procedure is completed, being inexpensively constructed of few, reliable, mostly plastic parts, the instrument may be disposed of in a manner avoiding contaminating or infecting others.

The instrument may also be employed to take biopsy specimens of other soft tissues throughout the body, for example specimens from the lung, liver, kidney, thyroid, breast or muscle.

Figure 4A:
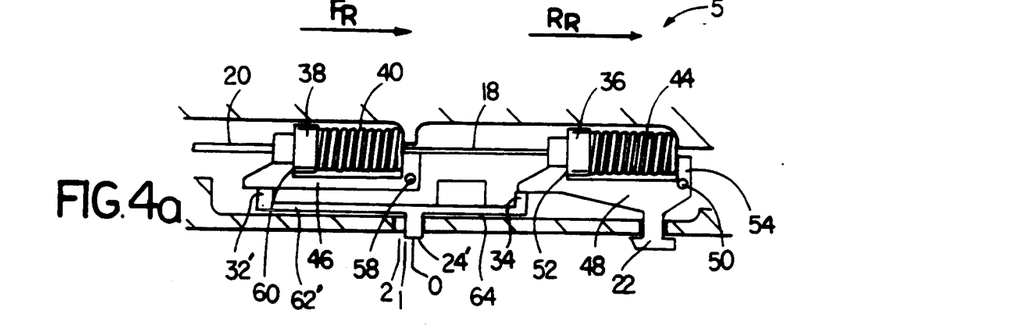
FIGS. 4(a) through 4(d) are cross-sectional side views of the firing mechanism of another embodiment of the invention which permits the separate projection of stylet and cannula, in FIG. 4a the selector switch is in a first safety position.

Referring to FIG. 4a et seq. in a simple modification of the device just described may be used to advantage for certain other tissues. In this embodiment, a selector switch 24' has an additional intermediate position termed "1". In this embodiment, the forward arm 62' of the selector switch 24' is shorter than the forward arm 62 in the previously described embodiment so that when selector switch 24' is moved forward to the position "1" (FIGS. 4b and 4c), the rear restraining projection 34 is moved far enough forward so as to permit the rear rocker arm 48 to pivot about pin 50, while the forward restraining projection 32' still prevents the forward rocker arm 46 from pivoting about pin 58. As the selector switch 24 is moved further forward to the position designated as "2" (FIG. 4d), the forward restraining projection 32' moves further forward and away from the forward rocker arm 46 and permits the forward rocker arm 46 to pivot about pin 58.

To project the stylet 18 and the cannula 20 separately, the selector switch 24' is slid into the intermediate position, termed "1". This moves the rear restraining projection 34 forward of the rearward rocker arm 48 permitting the rearward rocker arm 48 to rotate counterclockwise (arrow $P_R$) about pin 50. However, due to the unequal length of the arms, the forward restraining projection 32' remains in a position to prevent rocker arm 46 from rotating counterclockwise (arrow $P_F$) about pin 58.

Figure 4B:
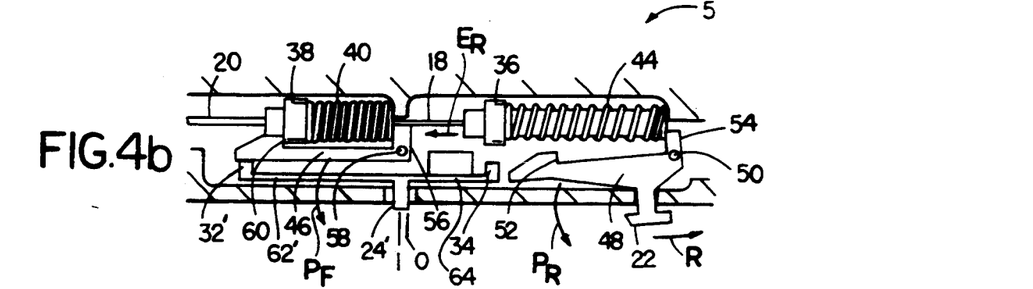

Referring to FIG. 4b, the stylet 18 is fired by pressing the firing button 22 rearwardly, (arrow R). Again this causes the rearward rocker arm 48 to rotate counterclockwise (arrow $P_R$) and move the latch portion 52 of the rearward rocker arm 48 away from the stylet retaining collar 36. This releases spring 44 which projects (arrow $E_R$) the stylet 18 and stylet retaining collar 36 forward.

Figure 4C:
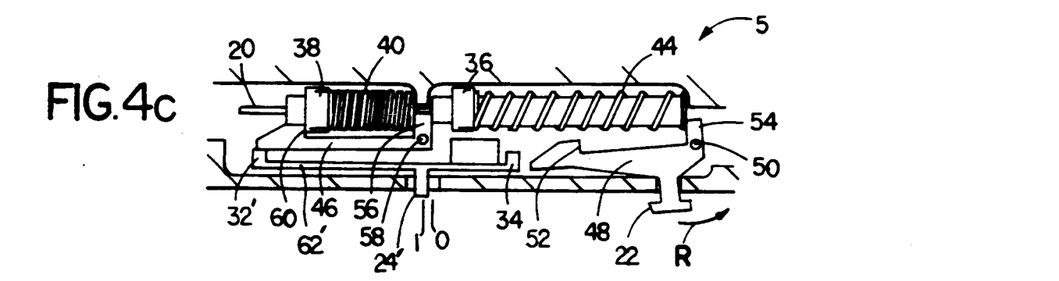

Referring to FIG. 4c, when the stylet retaining collar 36 hits the rear lever 56 of the forward rocker arm 46, the rear lever 56 is prevented from moving by the forward restraining projection 32'. This then prevents the forward rocker arm 46 from rotating counterclockwise. At this point the stylet 18 is fully extended but the cannula 20 has not been fired.

Figure 4D:
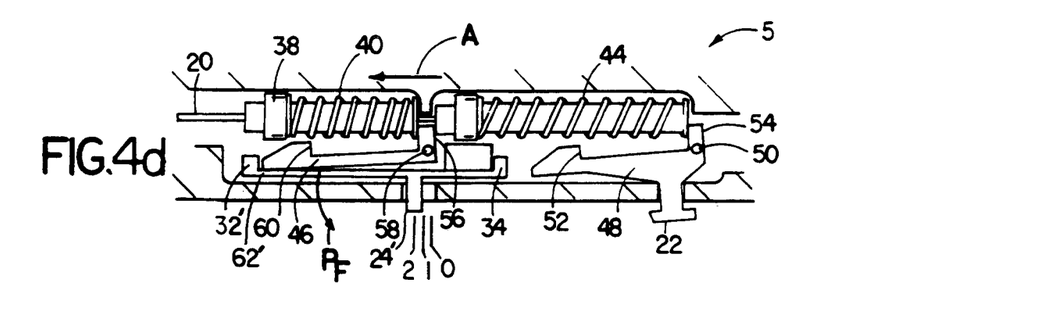

To fire the cannula 20, the selector switch 24' is then moved into the position "2" moving the forward restraining projection 32' forward and away from the forward rocker arm 46. Although the cannula 20 may now be fired, it will not fire spontaneously because the compressive force of spring 40 exceeds the expansion force of spring 44 on the rearward lever 56 of the forward rocker arm 46. This force-couple attempts to cause the rocker arm 46 to rotate clockwise and to cause the rearward lever 56 of the forward rocker arm 46 also to rotate clockwise. Therefore the latch portion 60 of the forward rocker arm is held against the cannula 46X retaining collar 38, holding the spring 40 in compression.

Referring to FIG. 4d, to fire the cannula 20, a forward force (arrow A) is applied to the rear loading slide switch 14. This forces the stylet retaining collar 36 further against the forward lever 56 and exceeds the compressive force of spring 40. This permits the forward rocker arm 46 to rotate counterclockwise (arrow $P_F$) away from the cannula retaining collar 38, releasing spring 40 and projecting the cannula retaining collar 38 and the cannula 20 forward.

To remove the biopsy sample once the cannula 20 has been fired, the cannula 20 and stylet 18 are withdrawn from the tumor and the cannula 20 is then retracted by rearwardly sliding the forward slide switch 12 to expose the tissue captured in the stylet notch 30 (FIG. 1c).

The benefit of the second embodiment is that if the stylet is projected and misses the tumor, the cannula need not be projected. The stylet can be reloaded separately and another attempt made to penetrate the tumor. In this way there is no unnecessary severing of healthy tissue by the cannula.

Advantages of the invention can, of course, be realized with many other specific forms of the instrument. For instance in another embodiment of certain broad aspects of the invention, a single multiposition finger-operable slide member may be employed to selectively load the springs. This slide member is not only slidable along a longitudinal axis but also selectably rotatable about the axis between a number of positions, in at least two of which it is free to slide. It has projections for respective engagement with the retaining means for the cannula and stylet, depending upon the selected rotational position of the slide member, much in the nature of a gear shift device. Thus the physician may rotate the thumb tab portion of the slide member to a first selected rotatable position with a thumb of the hand that holds the instrument and with that thumb, draw back the slide member and load the cannula spring, retracting the cannula. Still with the same thumb he can return the slide forwardly, rotate it to a second selected position, and draw it back again to load the stylet spring, retracting the stylet. The physician can employ this loading device also to release the stylet which then snaps forward, which then releases the cannula as described above. Alternatively, a rotated latch position can be provided for the thumb tab of the slide member, e.g. by use of a notch in the housing, that will prevent release and thus serve as a latch. Alternatively, a separate latch member for the stylet and a firing button can be provided, as described above.

Having shown an illustrative embodiment, those skilled in the art will realize many variations are possible which will still be within the scope and spirit of the claimed invention. Therefore, it is the intention to limit the invention only as indicated by the scope of the claims.

What is claimed is:

1. A biopsy needle instrument comprising:
    a housing,
    extending from said housing, an axially elongated stylet having a distal end and a proximal end and defining a specimen-defining formation adjacent said distal end and a cannula coaxially disposed about said stylet, said cannula having a distal end and a proximal end,
    said stylet mounted for axial movement relative to said housing and relative to said cannula between a first, retracted position and a second, extended position,
    said cannula mounted for axial movement relative to said housing and relative to said stylet between a first, retracted position and a second, extended position,
    means for biasing said stylet distally toward said second, extended position,
    means for biasing said cannula distally toward said second, extended position,
    first finger-displaceable means for retracting said stylet from said second, extended position to said first, retracted position,
    separate and discrete second finger-displaceable means for retracting said cannula from said second extended position to said first retracted position,
    said instrument constructed to enable release of said stylet to allow said stylet to move from said first, retracted position to said second, extended position and thereafter release of said cannula to allow said cannula to move from said first, retracted position to said second, extended position,
    said first and second finger-displaceable means being located on a side of said housing in position to be directly, selectively engaged and displaced by a finger of a single hand while said hand holds the instrument.

2. The biopsy needle instrument of claim 1 incorporating respective compression springs as said means for biasing said stylet and said cannula, wherein said first and second finger-displaceable means comprise thumb-engageable longitudinally aligned slide members constructed and arranged to directly displace respective ends of said springs to selectively pull them into a compressed, retracted position by the thumb of a single hand that holds said instrument.

3. The biopsy needle instrument of claim 2 in which said finger-engageable slide members transmit their forces to respective members engaged directly on the ends of respective compression springs, said stylet and cannula directly attached respectively to said members.

4. The biopsy needle instrument of claim 1 wherein said finger-displaceable means are disposed in a recess in a side of said housing that enables finger access.

5. The biopsy needle instrument of claim 1, 2, 3 or 4 wherein said housing is of rectangular transverse cross-section, said finger-displaceable means being positioned along a relatively broad surface of said housing and a firing button located on a relatively narrow upwardly directed surface of said housing, said firing button located in position to be engaged by a finger of a single hand that holds said instrument.

6. The biopsy needle instrument of claim 5 including a pivotable latch for securing said stylet in retracted position, and said firing button comprises a lever extension of said latch.

7. The biopsy needle instrument of claim 1 further comprising a finger-operable lock member located on a surface of the housing, in position to be engaged by a finger of a single hand that holds the instrument, said lock member adapted for movement between a first locking position and a second release position, said lock member in said first position disposed to oppose release of said stylet and said cannula, and said lock member, in said second, release position, enabling release of said stylet and said cannula.

8. The biopsy needle instrument of claim 7 wherein said lock member comprises a slide element disposed for movement along an upwardly-directed surface of said housing.

9. The biopsy needle instrument of claim 1 including a stylet latch means for retaining said stylet in said first, retracted position, said latch means comprising a first rocker arm and a first pin, said first rocker arm adapted to rotate about said first pin between a first position and a second position, said first rocker arm, in said first position, adapted to retain said stylet in said first retracted position, and said first rocker arm, in said second position, adapted to release said stylet.

10. The biopsy needle instrument of claim 1 or 9 including a cannula latch means for retaining said cannula in said first, retracted position, said latch comprising a second rocker arm and a second pin, said second rocker arm adapted to rotate about said second pin between a first position and a second position, said second rocker arm, in said first position, adapted to retain said cannula in said first retracted position, and said second rocker arm, in said second position, adapted to release said cannula.

11. The biopsy needle instrument of claim 1 wherein said finger displaceable means for retracting said stylet comprises a first slide switch slidably mounted upon and extending through said housing and attached to a stylet retaining means, such that when said first slide switch is moved rearwardly, said stylet retracts from said second extended position to said first retracted position.

12. The biopsy needle instrument of claim 1 or 11 wherein said separate and discrete finger displaceable means for retracting said cannula comprises a second slide switch slidably mounted upon and extending through said housing and attached to a cannula retaining means, such that when said second slide switch is moved rearwardly, said cannula retracts from said second extended position to said first retracted position.

13. The biopsy needle instrument of claim 1 including means for releasing a stylet latch means that latches said stylet in retracted position, said means for releasing comprising a button extending from said housing and attached to said stylet latch means, such that when said button is actuated, said stylet latch means ceases to retain said stylet.

14. A biopsy needle instrument comprising:
a housing of rectangular transverse cross-section,
extending from said housing, an axially elongated stylet having a distal end and a proximal end and defining a specimen-defining formation adjacent said distal end and a cannula coaxially disposed about said stylet, said cannula having a distal end and a proximal end,
said stylet mounted for axial movement relative to said housing and relative to said cannula between a first, retracted position and a second, extended position,
said cannula mounted for axial movement relative to said housing and relative to said stylet between a first, retracted position and a second, extended position,
stylet retaining means at the proximal end of said stylet and disposed in said housing, wherein said stylet retaining means comprises a collar attached to said stylet,
cannula retaining means at the proximal end of said cannula and disposed in said housing, wherein said cannula retaining means comprises a collar attached to said cannula,
means for biasing said stylet distally toward said second, extended position, wherein said bias means for said stylet comprises a compression spring,
means for biasing said cannula distally toward said second, extended position, wherein said bias means for said cannula comprises a compression spring,
said stylet retaining means and said cannula retaining means bearing on ends of said respective compression springs,
stylet latch means for retaining said stylet in said first, retracted position,
cannula latch means for retaining said cannula in said first retracted position,
means on a relatively broad side of said rectangular cross-section housing for retracting said stylet from said second, extended position to said first, retracted position for engagement of said stylet latch means to retain said stylet in retracted position against the means for biasing the stylet distally, wherein said means for retracting said stylet comprises a first slide switch slidably mounted upon and extending through said housing and attached to said stylet retaining means, such that when said first slide switch is moved rearwardly, said stylet retracts from said second extended position to said first retracted position,
separate and discrete means on the same relatively broad side of said rectangular cross-section housing for retracting said cannula from said second, extended position to said first, retracted position for engagement of said cannula latch means to retain said cannula in retracted position against the means for biasing the cannula distally, wherein said separate and discrete means for retracting said cannula comprises a second slide switch slidably mounted upon and extending through said housing and attached to said cannula retaining means, such that when said second slide switch is moved rearwardly, said cannula retracts from said second extended position to said first retracted position
and means for releasing said stylet latch means to allow said stylet to move from said first, retracted position to said second, extended position and thereafter releasing said cannula latch means to allow said cannula to move from said first, retracted position to said second, extended position.

15. The biopsy needle of claim 14 wherein said means for releasing said stylet latch means comprises a button extending from a relatively narrow side of said housing and attached to said stylet latch means, such that when said button is actuated, said stylet latch means ceases to retain said stylet.

16. The biopsy needle instrument of claim 14 wherein said stylet latch means for retaining said stylet in said first, retracted position, comprises a first rocker arm and a first pin, said first rocker arm adapted to rotate about said first pin between a first position and a second position, said first rocker arm, in said first position, adapted to engage said stylet retaining means and to retain said stylet in said first retracted position, and said first rocker arm, in said second position, spaced from engagement with said stylet retaining means.

17. The biopsy needle instrument of claim 14 or 16 wherein said cannula latch means for retaining said cannula in said first retracted position, comprises a second rocker arm and a second pin, said second rocker arm adapted to rotate about said second pin between an first position and a second position, said second rocker arm, in said first position, adapted to engage said cannula retaining means to retain said cannula in said first retracted position, and said second rocker arm, in said second position, spaced from engagement with said cannula retaining means.

18. A biopsy needle instrument comprising:
a housing,
extending from said housing, an axially elongated stylet having a distal end and a proximal end and defining a specimen-defining formation adjacent said distal end and a cannula coaxially disposed about said stylet, and said cannula having a distal end and a proximal end, said stylet mounted for axial movement relative to said housing and relative to said cannula between a first, retracted position and a second, extended position, said cannula mounted for axial movement relative to said housing and relative to said stylet between a first, retracted position and a second, extended position, means for biasing said stylet distally toward said second, extended position, means for biasing said cannula distally toward said second, extended position, finger displaceable slide means operable for selective independent retracting of said stylet and said cannula from their respective second, extended positions to their respective first, retracted positions, said finger displaceable slide means being located on a side of said housing in position to be directly, selectively engaged and slidably displaced by a finger of a single hand while said hand holds said instrument, said instrument constructed to enable release of said stylet to allow said stylet to move from said first, retracted position to said second, extended position and thereafter release of said cannula to allow said cannula to move from said first, retracted position to said second, extended position, said finger-displaceable slide means being located on a side of said housing in position to be directly, selectively engaged and slidably displaced by a finger of a single hand while said hand holds the instrument.

19. A method of taking a tissue sample comprising the steps of:

providing a biopsy needle instrument comprising a housing, extending from said housing an axially elongated stylet having a distal end and a proximal end and defining a specimen-defining formation adjacent said distal end and a cannula coaxially disposed about said stylet, said cannula having a distal end and a proximal end, said stylet mounted for axial movement relative to said housing and relative to said cannula between a first, retracted position and a second, extended position, said cannula mounted for axial movement relative to said housing and relative to said stylet between a first, retracted position and a second, extended position, means for biasing said stylet distally toward said second, extended position, means for biasing said cannula distally toward said second, extended position, finger-displaceable means operable for selective independent retracting of said stylet from said second, extended position to said first, retracted position and of said cannula from said second, extended position to said first, retracted position, said instrument constructed to enable release of said stylet to allow said stylet to move from said first, retracted position to said second, extended position and thereafter release of said cannula to allow said cannula to move from said first, retracted position to said second, extended position, said finger-displaceable means being located on a side of said housing in position to be directly selectively engaged and displaced by a finger of a single hand while that hand holds the instrument, while holding said instrument with a single hand:

retracting said stylet from a second, extended position to a first, retracted position with a finger of said single hand, retracting said cannula from a second, extended position to a first, retracted position with a finger of said single hand, positioning said stylet so as to allow said stylet to project into the tissue to be sampled, releasing said stylet with a finger of said single hand to allow said stylet to move from said first, retracted position to said second, extended position and said cannula to move from said first, retracted position to said second, extended position, thereby severing a sample of tissue;

and withdrawing said stylet and cannula together from the tissue.

20. The method of claim 19 wherein said finger-displaceable means comprises a pair of finger-operable slide switches respectively associated with said stylet and said cannula, each being moved independently in sequence.

21. The method of claim 20 wherein said slide switches are longitudinally aligned, said method including, while holding said instrument in a single hand, adjusting the position of the hand on the instrument between forward and rearward positions to respectively position the thumb to draw back the respective front and rear thumb switches, and respectively drawing back said thumb switches.

22. A method of examination by a physician comprising the physician grasping with one hand an ultrasound probe and conducting an ultrasound examination of a patient, grasping with the other hand a biopsy needle instrument comprising telescoped stylet and cannula, each associated with a spring drive means, means to compress the spring drive means, means to hold the spring drive means in compressed condition and means to actuate the spring drive means to fire the telescoped stylet and cannula in sequence, the instrument being constructed for single handed operation, and, the physician, with the single hand, compressively loading the spring drive means, positioning the instrument to take a specimen, firing said instrument to take a specimen, removing the instrument from the patient and, still with said single hand, compressively loading the cannula spring to expose the specimen for deposit.

23. The method of claim 22 including, after depositing a first specimen, repeating said loading, positioning and firing said instrument all one-handedly to take a further specimen.

* * * * *

UNITED STATES PATENT AND TRADEMARK OFFICE
CERTIFICATE OF CORRECTION

PATENT NO.    : 5,368,045

DATED         : November 29, 1994

INVENTOR(S)   : Thomas P. Clement et al.

It is certified that error appears in the above-identified patent and that said Letters Patent is hereby corrected as shown below:

Cover page, in [56] References Cited, FOREIGN PATENT DOCUMENTS, "delete 010321 10/1979 European Pat. Off.", "141108 1/1950 Germany", and "WO8300112 1/1983 WIPO".

Cover page, in [56] References Cited, FOREIGN PATENT DOCUMENTS delete "48382 2/1970 Germany"

Cover page, in [56] References Cited, OTHER PUBLICATIONS, Microvasive-Brochure, Van Tec Products is duplicated.

Col. 2, line 2, "Stiff" should be --stiff--.

Col. 2, line 52, after "EMBODIMENTS" insert a paragraph ard center "STRUCTURE".

Col. 3, line 58, "$C_F$♦" should be --$C_F$--.

Col. 10, claim 17, line 54 "an" should be --a--.

Signed and Sealed this

Seventh Day of May, 1996

BRUCE LEHMAN

Attest:

Attesting Officer

Commissioner of Patents and Trademarks